(12) United States Patent
Ashida et al.

(10) Patent No.: US 9,039,603 B2
(45) Date of Patent: May 26, 2015

(54) PROPULSION APPARATUS AND DRIVE APPARATUS FOR ENDOSCOPE

(71) Applicant: FUJIFILM Corporation, Tokyo (JP)

(72) Inventors: Tsuyoshi Ashida, Ashigarakami-gun (JP); Takayuki Nakamura, Ashigarakami-gun (JP); Nobuyuki Torisawa, Ashigarakami-gun (JP); Takumi Dejima, Ashigarakami-gun (JP); Naoyuki Morita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/750,446

(22) Filed: Jan. 25, 2013

(65) Prior Publication Data

US 2013/0197307 A1     Aug. 1, 2013

(30) Foreign Application Priority Data

Jan. 27, 2012   (JP) ................. 2012-014977

(51) Int. Cl.
| | |
|---|---|
| *A61B 1/00* | (2006.01) |
| *A61B 1/04* | (2006.01) |
| *A61M 31/00* | (2006.01) |
| *A61M 37/00* | (2006.01) |
| *G01N 21/00* | (2006.01) |

(52) U.S. Cl.
CPC ........... *A61B 1/0016* (2013.01); *A61B 1/00006* (2013.01)

(58) Field of Classification Search
USPC ................. 600/104, 106, 114–116, 127, 129; 604/95.01–95.05, 264, 271; 356/241.1–241.6
See application file for complete search history.

(56) References Cited

U.S. PATENT DOCUMENTS

| | | | |
|---|---|---|---|
| 2005/0272976 A1 | 12/2005 | Tanaka et al. | |
| 2007/0239140 A1* | 10/2007 | Chechelski et al. | ............... 606/1 |
| 2009/0233747 A1* | 9/2009 | Sheridan et al. | ................ 475/12 |
| 2010/0021234 A1* | 1/2010 | Willis et al. | ..................... 404/90 |
| 2010/0210900 A1* | 8/2010 | Allen et al. | ................... 600/101 |

FOREIGN PATENT DOCUMENTS

JP     2005-253892 A     9/2005

* cited by examiner

*Primary Examiner* — Ryan Henderson
(74) *Attorney, Agent, or Firm* — Birch, Stewart, Kolasch & Birch, LLP

(57) ABSTRACT

A propulsion apparatus for an endoscope includes a propulsion assembly for mounting on a tip device of the endoscope, for propulsion in a body cavity. First and second wire devices are disposed to extend from the tip device in a proximal direction, having a coil winding, for rotating to drive the propulsion assembly. First and second motors are connected with proximal ends of respectively the first and second wire devices, for rotating the first and second wire devices. A timer is actuated if a speed difference between rotational speeds of the first and second motors becomes equal to or more than a reference speed value, for measuring an elapsed time. A break detector detects breakage of the first wire device if the elapsed time becomes equal to or longer than a predetermined time. A controller controls the first and second motors in response to an output of the break detector.

13 Claims, 13 Drawing Sheets

PROPULSION APPARATUS AND DRIVE APPARATUS FOR ENDOSCOPE

BACKGROUND OF THE INVENTION

1. Field of the Invention

The present invention relates to a propulsion apparatus and a drive apparatus for an endoscope. More particularly, the present invention relates to a propulsion apparatus for an endoscope in which breakage of a wire device can be detected reliably and also operability for propulsion can be maintained, and a drive apparatus for the endoscope.

2. Description Related to the Prior Art

An endoscope is an instrument in the medical field for diagnosis and treatment. The endoscope has an elongated tube and a tip device at a distal end. A CCD or the like is incorporated in the tip device and entered in a body cavity of a patient's body. An image is obtained by the CCD, displayed on a display panel, and viewed for diagnosing the body cavity.

A propulsion assembly for propelling an elongated tube of the endoscope has been suggested recently. U.S. Ser. No. 2005/272,976 (corresponding to JP-A 2005-253892) discloses the propulsion assembly including a support sleeve and an endless track device. The support sleeve is mounted on the tip device of the endoscope. The endless track device is endlessly movable around the support sleeve. An outer run (working run) of the endless track device contacts a wall of a gastrointestinal tract and is traveled, so that the endless track device moves the tip device of the endoscope in a distal direction through the gastrointestinal tract more deeply according to friction of the endless track device with the wall. It is effective in facilitating entry of the endoscope into the gastrointestinal tract of a tortuous form, such as a large intestine, even with low skill in the manipulation of the endoscope.

In U.S. Ser. No. 2005/272,976, wire devices are rotated by motors. A magnet bar is connected at a distal end of the wire devices, and is rotated to move the endless track device endlessly as an extension between magnet rollers. The magnet bar is in a form of windings of which the N and S poles are arranged alternately, and operates as a worm gear. The magnet roller has the N and S poles, and operates as a worm wheel. The wire devices are likely to break with time due to metal fatigue. The endless track device cannot be moved upon breakage of the wire devices. There arises a problem of failure in removal of the propulsion assembly from out of the gastrointestinal tract.

By use of a plurality of the wire devices and a plurality of the motors, the endless track device is still movable by a remaining one of the wire devices when a first one of the wire devices is broken. It is possible to conceive a fail-safe function by detection of breakage of the wire devices. The motors are controlled when the wire devices are broken, for example, the motors are stopped, or driven for moving the endless track device in the proximal direction to eliminate the tip device of the endoscope from the gastrointestinal tract. To this end, rotational speeds of the motors are detected. A speed difference between those is obtained and evaluated to detect breakage of one of the wire devices.

However, the speed difference is likely to occur when the wire devices are flexed, because the rotational speed of the motors is decreased by an increase in the rotational load of the wire devices. Furthermore, resonance vibration of the motors in rotation may occur due to a moment of inertia of the motors and torsional rigidity of the wire devices according to a change in the speed with the flexure of the wire devices. The speed difference of the motors is likely to remain. A problem of poor operability for the propulsion arises when the endless track device is stopped upon detecting breakage of the wire devices with the change in the speed due to the resonance vibration of the wire devices.

SUMMARY OF THE INVENTION

In view of the foregoing problems, an object of the present invention is to provide a propulsion apparatus for an endoscope in which breakage of a wire device can be detected reliably and also operability for propulsion can be maintained, and a drive apparatus for the endoscope.

In order to achieve the above and other objects and advantages of this invention, a propulsion apparatus for an endoscope includes a propulsion assembly for mounting on a tip device of the endoscope, for propulsion in a body cavity. First and second wire devices are disposed to extend from the tip device in a proximal direction, for driving the propulsion assembly. First and second motors are connected with proximal ends of respectively the first and second wire devices, for generating torque for actuating the propulsion assembly. A monitoring unit is actuated if a speed difference between the first and second motors becomes equal to or more than a reference speed value, for measuring an elapsed time. A break detector detects breakage of the first or second wire device if the elapsed time becomes equal to or longer than a predetermined time. A controller controls the first and second motors in response to detection of the break detector.

The first and second wire devices have a coil winding.

The reference time is equal to or longer than a half of a resonance period of the first and second motors.

The monitoring unit includes a speed measuring device for measuring rotational speeds of the first and second motors. A combining circuit acquires the speed difference arithmetically. A first comparator detects becoming of the speed difference equal to or more than the reference speed value in relation to breakage of the first wire device. A first timer measures the elapsed time in response to an output of the first comparator.

The monitoring unit further includes an inverter for inverting a sign of the speed difference to obtain a second speed difference. A second comparator detects becoming of the second speed difference equal to or more than a reference speed value in relation to breakage of the second wire device. A second timer measures the elapsed time in response to an output of the second comparator.

If the first or second wire device is broken, the controller stops the first and second motors.

In another preferred embodiment, if one of the first and second wire devices is broken, the controller drives the first or second motor to move the tip device to an outside of the body cavity.

Furthermore, a first drive device drives the first motor by applying drive energy thereto. A second drive device drives the second motor by applying drive energy thereto. A servo control unit is connected with the speed measuring device, for feedback control of the first and second drive devices according to the rotational speeds being measured, to adjust the drive energy.

Furthermore, an alarm device informs the breakage of the first wire device in response to the output of the break detector.

The propulsion assembly includes a support sleeve for receiving entry of the tip device. A barrel sleeve is disposed around the support sleeve. An endless track device is disposed to extend along inner and outer surfaces of the barrel sleeve, for contacting a wall of the body cavity, and endlessly moving in an axial direction of the endoscope. A driving mechanism is connected with the first and second wire devices, for driving the endless track device upon actuation of the first and second motors.

The endless track device is disposed to extend circumferentially around the barrel sleeve in a toroidal form.

In still another preferred embodiment, the endless track device includes a plurality of endless belts disposed to cover the barrel sleeve partially.

The propulsion assembly includes a drive sleeve, contained in the support sleeve in a rotatable manner, and having spur gear teeth formed on an outer surface thereof. First and second coupling gears are connected with distal ends of respectively the first and second wire devices, for rotating the drive sleeve with the spur gear teeth.

The propulsion assembly further includes a sealing device for fastening the support sleeve to the tip device of the endoscope.

The propulsion assembly includes a plurality of idler rollers, supported on the barrel sleeve in a rotatable manner, for contacting an internal surface of the endless track device. The driving mechanism includes worm gear teeth formed on the outer surface of the drive sleeve. A plurality of wheels are supported on the support sleeve in a rotatable manner, meshed with the worm gear teeth, for driving the endless track device contacted by the idler rollers.

Also, a propulsion apparatus for an endoscope includes a propulsion assembly for mounting on a tip device of the endoscope, for propulsion in a body cavity. First and second wire devices are disposed to extend from the tip device in a proximal direction, having a coil winding, for rotating to drive the propulsion assembly. First and second motors are connected with proximal ends of respectively the first and second wire devices, for rotating the first and second wire devices. A timer is actuated if a speed difference between rotational speeds of the first and second motors becomes equal to or more than a reference speed value, for measuring an elapsed time. A break detector detects breakage of the first wire device if the elapsed time becomes equal to or longer than a predetermined time. A controller controls the first and second motors in response to an output of the break detector.

The reference time is equal to or longer than a half of a resonance period of resonance vibration of the first and second motors.

Furthermore, a speed measuring device measures the rotational speeds of the first and second motors. A combining circuit acquires the speed difference between the rotational speeds. A first comparator is connected between the combining circuit and the timer, for detecting becoming of the speed difference equal to or more than the reference speed value.

If the first wire device is broken, the controller stops the first and second motors.

In another preferred embodiment, if the first wire device is broken, the controller drives the second motor to move the tip device to an outside of the body cavity.

Furthermore, an inverter inverts a sign of the speed difference to obtain a second speed difference. A second comparator compares the second speed difference with a reference speed value, and causes the timer to operate if the second speed difference becomes equal to or more than the reference speed value, to measure a second elapsed time. The break detector detects breakage of the second wire device if the second elapsed time becomes equal to or longer than a predetermined time.

Also, a drive apparatus for an endoscope includes a drive assembly for mounting on a tip device of the endoscope. First and second wire devices are disposed to extend from the tip device in a proximal direction, for driving the drive assembly. First and second motors are connected with proximal ends of respectively the first and second wire devices, for generating torque for actuating the drive assembly. A monitoring unit is actuated if a speed difference between the first and second motors becomes equal to or more than a reference speed value, for measuring an elapsed time. A break detector detects breakage of the first or second wire device if the elapsed time becomes equal to or longer than a predetermined time. A controller controls the first and second motors in response to detection of the break detector.

Consequently, breakage of a wire device can be detected reliably and also operability for propulsion can be maintained, because the break detector cooperates with the timer and the controller and evaluates elapsed time to recognize the breakage suitably.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
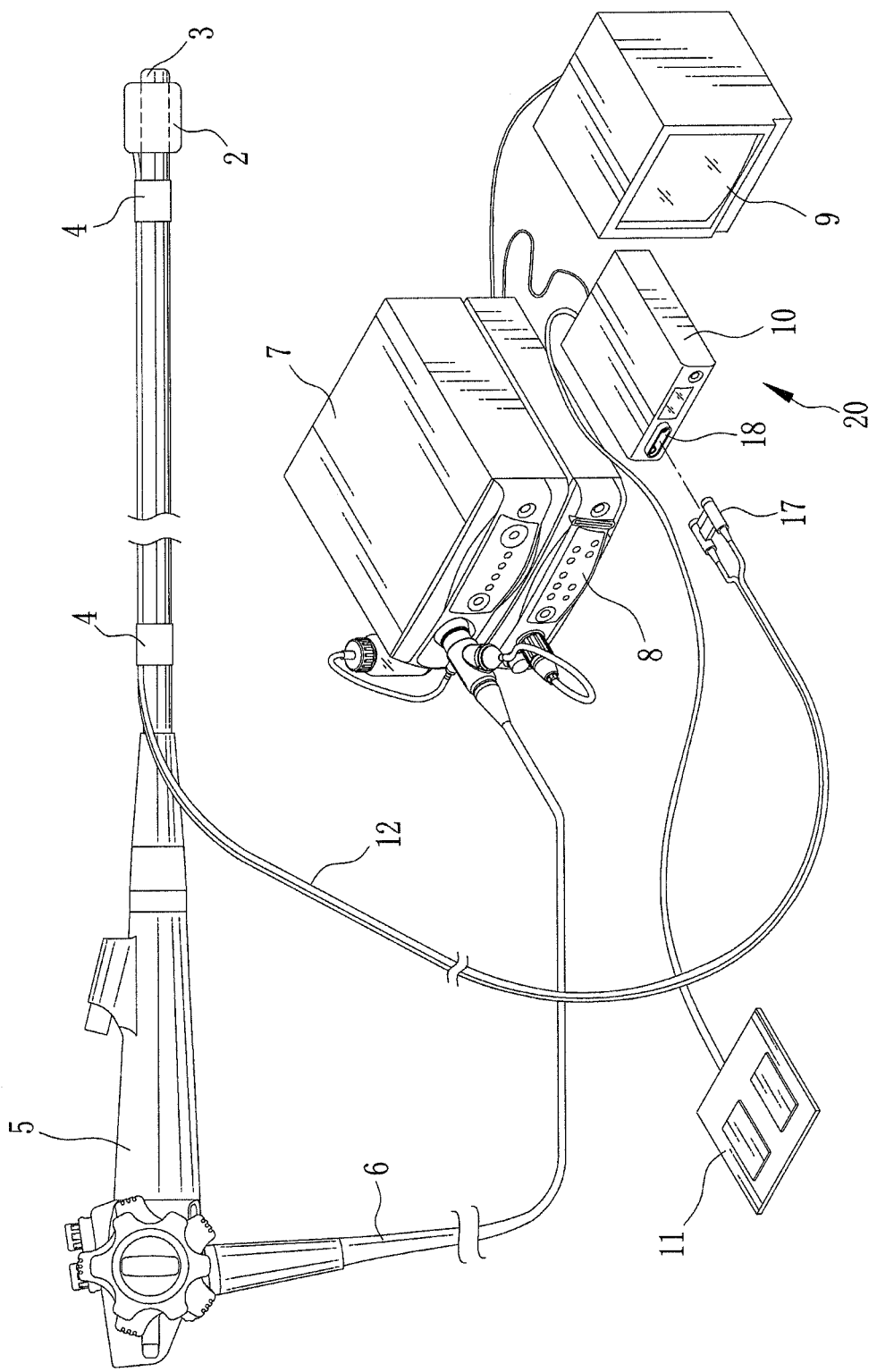
FIG. 1 is a perspective view illustrating an endoscope with a propulsion assembly.

In FIG. 1, a propulsion assembly 2 is for use with an endoscope. The propulsion assembly 2 is fitted around a tip device 3 of the endoscope. The endoscope includes an image sensor, lighting windows, a steering device, an elongated tube, a handle 5, steering wheels and the like. The image sensor is incorporated in the tip device 3, and is a CCD or CMOS image sensor. The lighting windows are formed in the tip device 3 and emit light. The image sensor images an object in a body cavity illuminated with the light from the lighting windows, such an object as a wall of a stomach or intestine of a gastrointestinal tract of a patient. The steering device is disposed at a proximal end of the tip device 3 for steering to enter the tip device 3 in the body cavity to reach the object.

The propulsion assembly 2 operates to facilitate the entry of the tip device 3. The steering wheels are disposed on the handle 5, and manually rotated to operate the steering device for bending up and down and to the right and left.

The handle 5 includes a button and an end sleeve. The button is operable to change over the supply and suction of air or water. The end sleeve has an instrument opening where a biopsy forceps or other medical device is advanced. A universal cable 6 extends from the handle 5, and connected to a light source apparatus 7 and a processing apparatus 8. Light from a lamp in the light source apparatus 7 is guided by a light guide fiber extending through the universal cable 6 and the endoscope to lighting windows. The processing apparatus 8 processes an image signal from the universal cable 6 in the signal processing suitably. A display panel 9 is driven to display the image of the image signal. The processing apparatus 8 discerns the type information of the endoscope for use according to the input information from the endoscope through the universal cable 6. The processing apparatus 8 automatically changes over the control and/or display suitably according to the type information, typically if the control with differences for the types is required in the course of the manipulation, or if the display with differences for the types is required on the display panel 9.

An actuating assembly 10 or controller is connected with the processing apparatus 8 electrically. The actuating assembly 10 actuates and controls the propulsion assembly 2. A wire sheath 12 of a dual lumen form extends from a proximal end of the propulsion assembly 2. An adhesive tape 4 or surgical tape positions the wire sheath 12 on the elongated tube of the endoscope at suitable points. The wire sheath 12 extends properly into the body cavity even upon moving the endoscope into the body cavity or during the manipulation.

First and second torque wire devices 15a and 15b are disposed to extend discretely through the wire sheath 12. Distal end portions of the wire devices 15a and 15b are coupled to a driving mechanism (sleeve) of the propulsion assembly 2. The wire devices 15a and 15b are flexible but have high torsional rigidity so that torque applied to their proximal end is transmitted by those to their distal end substantially without attenuation. A key coupling device 17 for plug-in is disposed at the proximal end of the wire devices 15a and 15b. A rotating coupling 18 for plug-in is disposed in the actuating assembly 10, and connected mechanically with the key coupling device 17. First and second motors 19a and 19b are incorporated in the actuating assembly 10. See FIG. 2. When the key coupling device 17 is plugged to the rotating coupling 18, the wire devices 15a and 15b are ready to rotate with respectively the first and second motors 19a and 19b. Structurally, a propulsion apparatus 20 is constituted by the propulsion assembly 2, the display panel 9, the actuating assembly 10 and the wire devices 15a and 15b.

Figure 2:
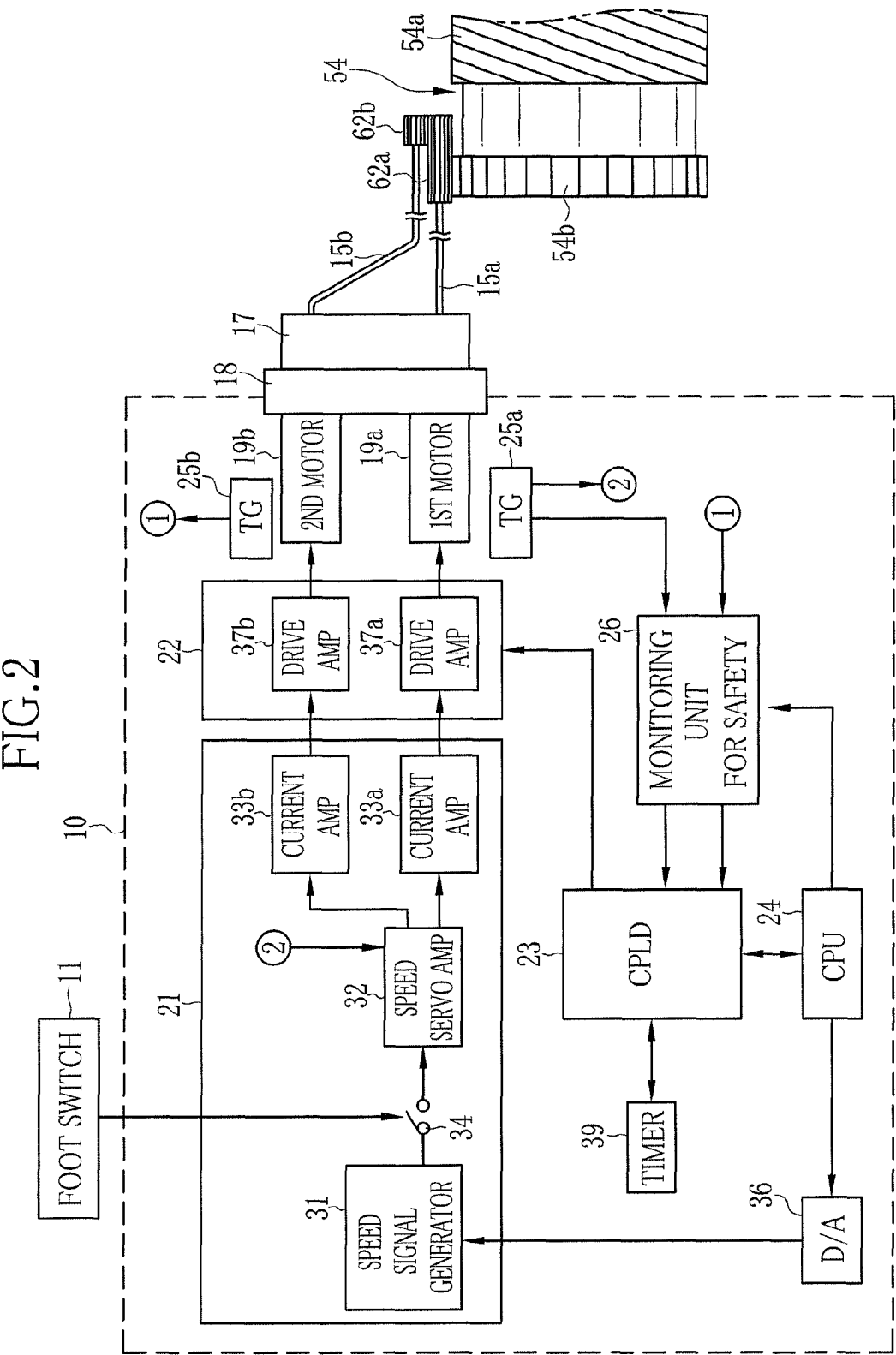
FIG. 2 is a block diagram schematically illustrating circuit elements in a propulsion apparatus.
Figure 3:
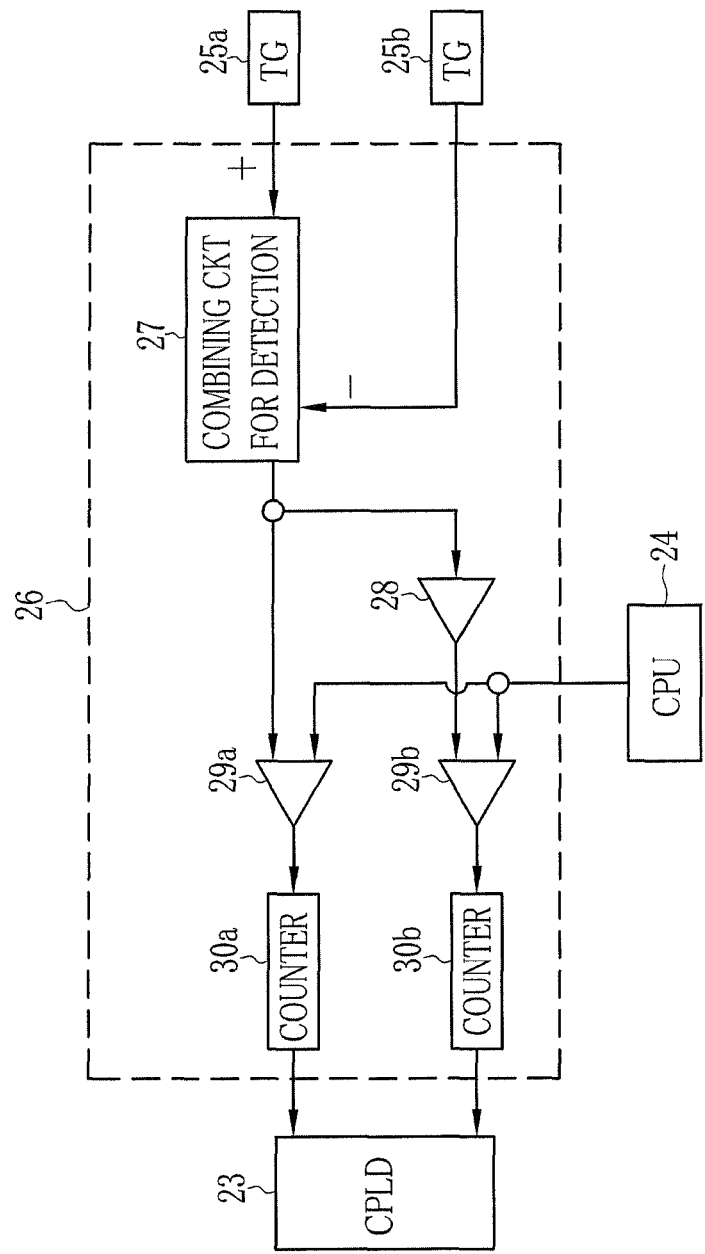
FIG. 3 is a block diagram schematically illustrating a monitoring unit for safety (difference detector)

In FIGS. 2 and 3, the actuating assembly 10 includes a servo control unit 21, a drive circuit board 22, a CPLD or complex programmable logic device 23 as a break detector, and a CPU 24. First and second tachogenerators 25a and 25b as a speed measuring device are incorporated in the actuating assembly 10 and detect rotational speeds of the first and second motors 19a and 19b. A monitoring unit 26 for safety or difference detector detects a difference between the rotational speeds of the first and second motors 19a and 19b.

The first and second tachogenerators 25a and 25b detect respectively rotational speeds of the first and second motors 19a and 19b, and send voltage signals to the monitoring unit 26 according to the rotational speeds. The monitoring unit 26 includes a combining circuit 27 for detection (subtractor), and an inverter 28. The combining circuit 27 detects a speed difference between the rotational speeds according to the voltage signals input by the first and second tachogenerators 25a and 25b, namely, subtracts the rotational speed of the second motor 19b from that of the first motor 19a. The inverter 28 changes the positive and negative signs of the speed difference obtained by the combining circuit 27. The monitoring unit 26 includes comparators 29a and 29b and counters 30a and 30b. Each of the comparators 29a and 29b compares the detected speed difference with a reference speed value set by the CPU 24. The counters 30a and 30b (timers) measure time.

A D/A converter 36 is connected with the CPU 24. A speed signal generator 31 is controlled by the CPU 24 with the D/A converter 36. The CPU 24 outputs information of a rotational speed to the speed signal generator 31 for effectively operating the propulsion apparatus 20, for example, 2,000 rpm. The reference speed value which is output by the CPU 24 to the monitoring unit 26 must be lower than the rotational speed of the first motor 19a, for example, 400 rpm.

When the speed difference becomes equal to or more than 400 rpm, a relevant one of the comparators 29a and 29b sends a count signal to a corresponding one of the counters 30a and 30b. The counters 30a and 30b start measuring time upon receiving the count signal. Although elapsed time is measured during continuous reception of the count signal, the counters 30a and 30b reset the elapsed time upon stop of the reception of the count signal. If the elapsed time becomes equal to or longer than a half of a resonance period determined by the torsional rigidity of the wire devices and the moment of inertia of the motors, then it is judged that a corresponding one of the wire devices 15a and 15b has broken. A break signal of the breakage is sent to the CPLD 23. Note that the reference time for evaluating the breakage of the wire devices may be suitably set in a manner different from the half of the resonance period. However, it is preferable to predetermine the reference time equal to or longer than the half of the resonance period.

The servo control unit 21 includes the speed signal generator 31, a speed servo amplifier 32, and first and second current amplifiers 33a and 33b or servo amplifiers. An on/off switch 34 is incorporated in the servo control unit 21 for switching between the speed signal generator 31 and the speed servo amplifier 32. There is an externally operable foot switch 11. The on/off switch 34 is shifted upon depressing the foot switch 11 and changes over connection and disconnection between the speed signal generator 31 and the speed servo amplifier 32.

When the speed servo amplifier 32 is connected to the speed signal generator 31 by closing the on/off switch 34, the speed signal generator 31 sends a speed signal to the speed servo amplifier 32 for a rotational signal determined by the CPU 24 with the D/A converter 36. The speed servo amplifier 32 sends a torque signal to the first and second current amplifiers 33a and 33b according to the input speed signal. Drive amplifiers 37a and 37b (drive devices) are incorporated in the drive circuit board 22, and connected respectively with the first and second current amplifiers 33a and 33b. The first and second current amplifiers 33a and 33b send current signals to the drive amplifiers 37a and 37b according to the input torque signal. The drive amplifiers 37a and 37b supply the first and second motors 19a and 19b with currents according to the input current signals. The speed servo amplifier 32 is supplied with information of a rotational speed detected by the first tachogenerator 25a, and controls the torque signal for the first current amplifier 33a according to the detected rotational speed in the feedback control.

Current detectors (not shown) detect the currents flowing across respectively the first and second motors 19a and 19b. The first and second current amplifiers 33a and 33b are supplied with the currents detected by the current detectors, and control the current signals directed to the drive amplifiers 37a and 37b according to the feedback control by use of information of the detected currents.

The CPLD 23 upon receiving a break signal from any one of the counters 30a and 30b sends a stop signal to a corresponding one of the drive amplifiers 37a and 37b in the drive circuit board 22. Responsively, any of the drive amplifiers 37a and 37b stops one of the first and second motors 19a and 19b by discontinuing supply of currents. Also, the CPLD 23 drives the display panel 9 as an alarm device to display information of breakage. When the speed difference detected by the monitoring unit 26 becomes smaller than the reference speed value, the CPLD 23 resets the counters 30a and 30b. Also, an auxiliary timer 39 measures time.

Figure 4:
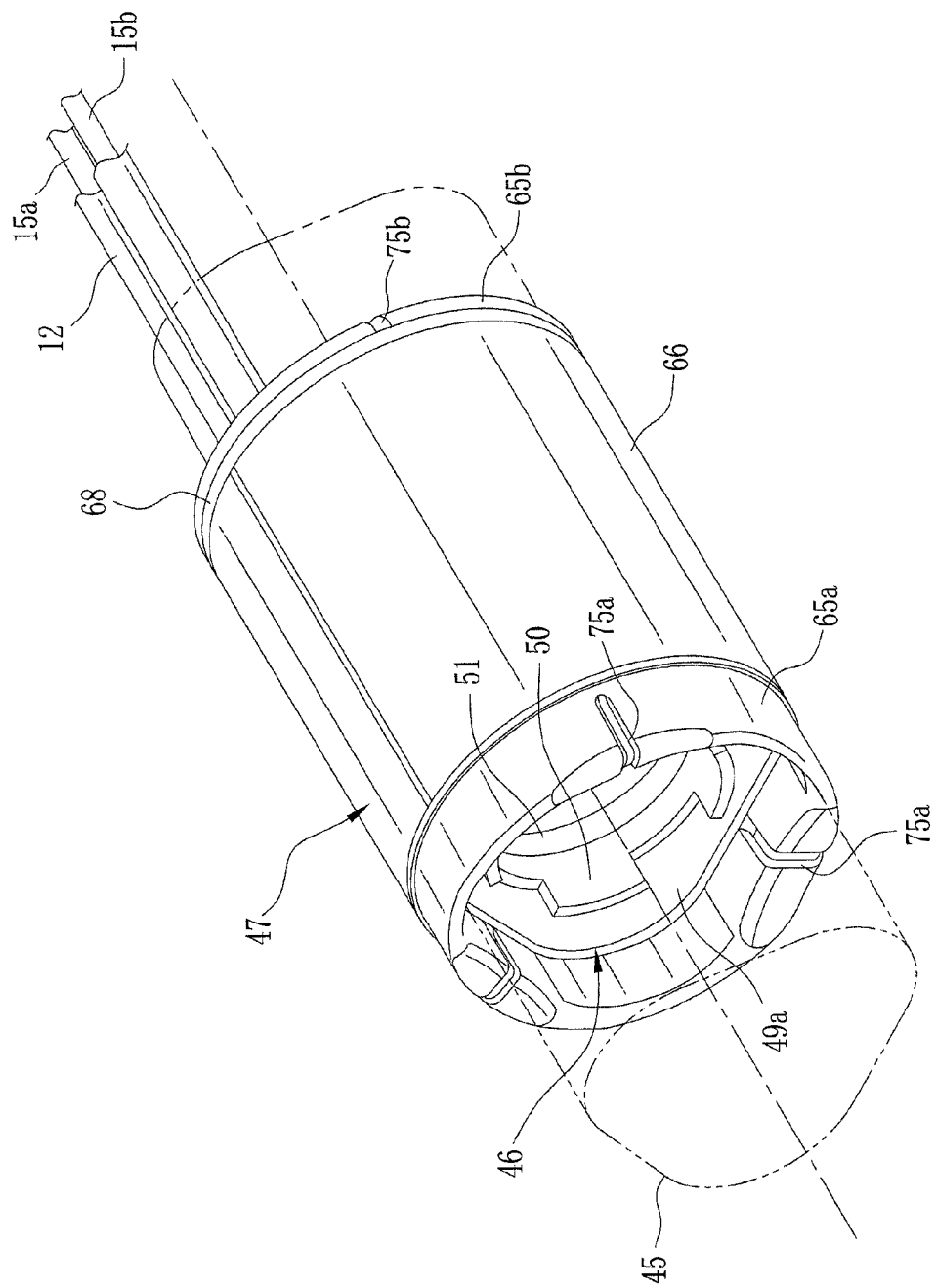
FIG. 4 is a perspective view illustrating the propulsion assembly.
Figure 5:
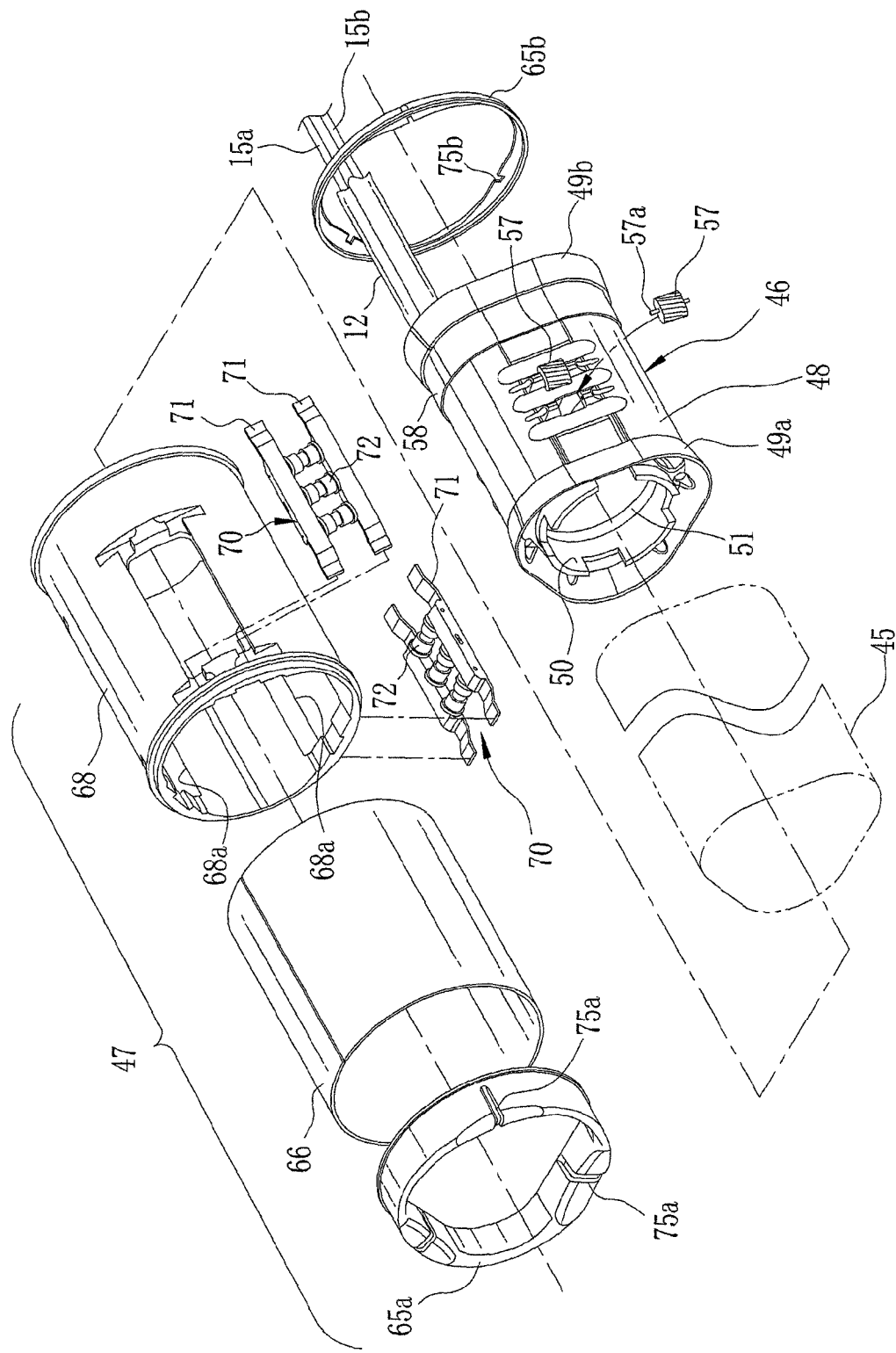
FIG. 5 is an exploded perspective view illustrating the propulsion assembly.

The propulsion apparatus 20 is used effectively specially for colonoscopy, because of manipulation for advance and pull in the sigmoid colon or transverse colon. The propulsion assembly 2 of the propulsion apparatus 20 is substantially cylindrical. An endless track device 45 or membrane or toroidal device is disposed on the outside of the propulsion assembly 2, is constituted by a flexible sheet of synthetic resin with sufficient rigidity. In FIGS. 4 and 5, the endless track device 45 is depicted in a developed form of a sleeve for understanding. A final form of the endless track device 45 is in a ring shape or toroidal shape after connecting front and rear ends of the sleeve. The endless track device 45 has an annular surface. See FIG. 7. In FIGS. 4-7, a distal side for protruding the tip device 3 is depicted on the left side. A proximal side near to the handle 5 of the endoscope is depicted on the right side.

In FIGS. 4 and 5, the propulsion assembly 2 includes a drive unit 46 or inner unit, and a barrel unit 47 or outer unit. The drive unit 46 is disposed inside the endless track device 45. The barrel unit 47 is disposed around the drive unit 46. The drive unit 46 includes a support sleeve 48, a cap ring 58, a distal cover flange 49a for wiping, a proximal cover flange 49b for wiping, a clamping sleeve 50 or collet sleeve, a sealing device 51 (in a C-shape) or C-ring or collet head, and a drive sleeve 54 in FIG. 6. The support sleeve 48 has a cylindrical inner surface and an outer surface in a shape of a triangular prism. The cap ring 58 is in a triangular shape, and retained to a proximal end of the support sleeve 48 by a screw, press-fit or caulking. The cover flanges 49a and 49b are attached to respectively the distal end of the support sleeve 48 and the proximal end of the cap ring 58. The clamping sleeve 50 is helically engaged with a thread formed inside the support sleeve 48, and rotates to move in the axial direction. The sealing device 51 is formed from synthetic resin with resiliency, and has a diameter changeable by movement of the clamping sleeve 50 in the axial direction. The drive sleeve 54 is a driving mechanism supported inside the support sleeve 48 in a rotatable manner.

Figure 6:
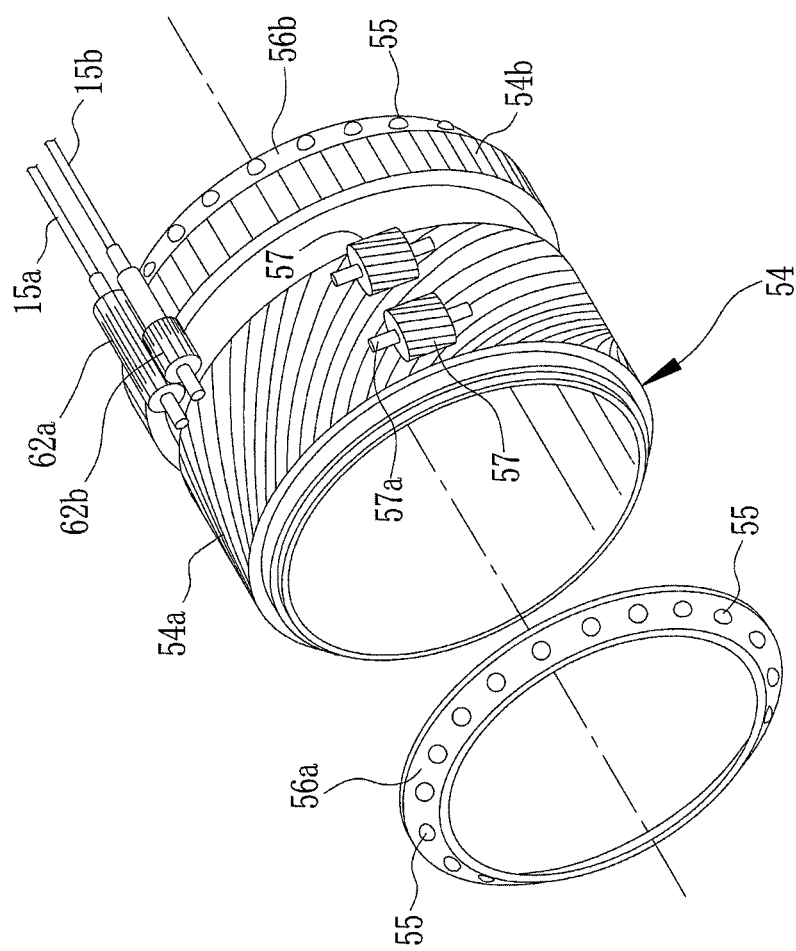
FIG. 6 is a perspective view illustrating a drive sleeve with coupling gears and worm wheels.

In FIG. 6, the propulsion assembly 2 includes bearing rings 56a and 56b, each of which is constituted by plural bearing balls 55 arranged annularly. The bearing rings 56a and 56b support ends of the drive sleeve 54 on an inner surface of the support sleeve 48 in a rotatable manner. The cap ring 58 is secured to a proximal end of the support sleeve 48, and prevents the drive sleeve 54 from dropping out. Worm gear teeth 54a or thread, and spur gear teeth 54b are arranged on an outer surface of the drive sleeve 54. Two rotatable worm wheels 57 or helical gears are supported on the support sleeve 48, and meshed with the worm gear teeth 54a through openings in the support sleeve 48. Three pairs of the worm wheels 57 are arranged equiangularly from one another around the drive sleeve 54. When the drive sleeve 54 rotates, the worm wheels 57 rotate around a gear shaft 57a in the same direction simultaneously.

A distal end of the wire sheath 12 is attached to the inside of the proximal end of the cap ring 58 by use of adhesion or thermal welding. Distal ends of first and second torque wire devices 15a and 15b protruding from the wire sheath 12 extend to pass through holes in the cap ring 58. First and second coupling gears 62a and 62b or pinions are firmly connected with distal ends of the wire devices 15a and 15b. As illustrated in the drawing, rotational shafts protrude from respectively the coupling gears 62a and 62b as rotational centers. The shafts are received in holes formed in the support sleeve 48, to keep the coupling gears 62a and 62b rotatable. Only the first coupling gear 62a of the first wire device 15a is meshed with the spur gear teeth 54b of the drive sleeve 54. The second coupling gear 62b of the second wire device 15b is meshed with the first coupling gear 62a but not with the spur gear teeth 54b. Thus, the drive sleeve 54 is driven by rotation of the first coupling gear 62a in connection with the first wire device 15a. However, the wire devices 15a and 15b are driven by torques generated by the actuating assembly 10. The second coupling gear 62b is rotated in a direction opposite to that of the first coupling gear 62a. The torque from the second wire device 15b is added to the torque of the first coupling gear 62a, so that the drive sleeve 54 can be rotated with a high torque.

Each of the cover flanges 49a and 49b includes a flange edge shaped to increase a width in the axial direction. The flange edge receives an inner surface of the endless track device 45 with closeness while the endless track device 45 turns around. The flange edge prevents various materials from pull into the propulsion assembly 2 together with the moving outer surface of the endless track device 45, the materials including foreign material and tissue of a body part.

A distal end of the clamping sleeve 50 has a pattern of projections and recesses arranged in the circumferential direction. A special screw driving device for the clamping sleeve 50 is entered for engagement with the clamping sleeve 50 in the proximal direction. The clamping sleeve 50 is rotated in a predetermined direction by the screw driving device, and thus shifts in the proximal direction. A tapered end surface 50a of the clamping sleeve 50 in FIG. 7 presses the sealing device 51, which deforms to decrease the diameter. Accordingly, an inner surface of the sealing device 51 is strongly pressed on a peripheral surface of the tip device 3 for firmly fitting the support sleeve 48 thereon.

The barrel unit 47 includes a distal support ring 65a or bumper ring, a cover sheet 66 for shielding, a barrel sleeve 68 for supporting rollers, and a proximal support ring 65b or bumper ring, in a sequence in the proximal direction. The barrel unit 47 is combined with the drive unit 46 and the endless track device 45 according to the steps as follows.

In FIGS. 4 and 5, a sheet material for the endless track device 45 in a developed form is formed in a cylindrical shape. The drive unit 46 is positioned so that its outer surface is covered inside the cylindrical shape of the sheet material. The drive unit 46 with the endless track device 45 is entered in the barrel sleeve 68. Three holder openings 68a are formed in the barrel sleeve 68 to extend in the axial direction, and arranged equiangularly from one another with 120 degrees. Roller mechanisms 70 are mounted in respectively the holder openings 68a.

In FIGS. 4-9, the roller mechanisms 70 include three idler rollers 72, and a pair of roller supports 71 or frames for supporting the idler rollers 72 in alignment. The roller supports 71 are resilient thin plates of metal, and are fixed to the barrel sleeve 68 by fitting their ends in end portions of the holder openings 68a. A center of the roller supports 71 in the longitudinal direction becomes curved to enter an inner space in the barrel sleeve 68 through the holder openings 68a. The idler rollers 72 supported by the roller supports 71 press the endless track device 45 toward the worm wheels 57 owing to the curved form of the roller supports 71. As a result, the endless track device 45 is tensioned tightly between the worm wheels 57 and the idler rollers 72. See FIG. 9. There is degree of freedom in one of the idler rollers 72 disposed at the center in relation to the longitudinal direction of the roller supports 71, because the center roller is supported by the opening extending longitudinally. A relative position of the endless track device 45 to two lateral rollers included in the idler rollers 72 is automatically adjusted for supporting the endless track device 45 with the worm wheels 57 in an optimally balanced manner.

The roller mechanisms 70 are fitted in the holder openings 68a fixedly on the barrel sleeve 68. The idler rollers 72 project to the inside of the barrel sleeve 68 and keep the barrel sleeve 68 immovable in the axial direction relative to the drive unit 46. The endless track device 45 is tensioned while the roller mechanisms 70 are combined with the barrel sleeve 68. The support rings 65a and 65b are fixed to respectively the distal and proximal ends of the barrel sleeve 68. Three grooves 75a are formed in the distal support ring 65a. Three grooves 75b are formed in the proximal support ring 65b. The grooves 75a and 75b are aligned with the roller mechanisms 70 in the axial direction. The cover sheet 66 tightly covers the outer surface of the barrel sleeve 68 together with the roller mechanisms 70.

Figure 7:
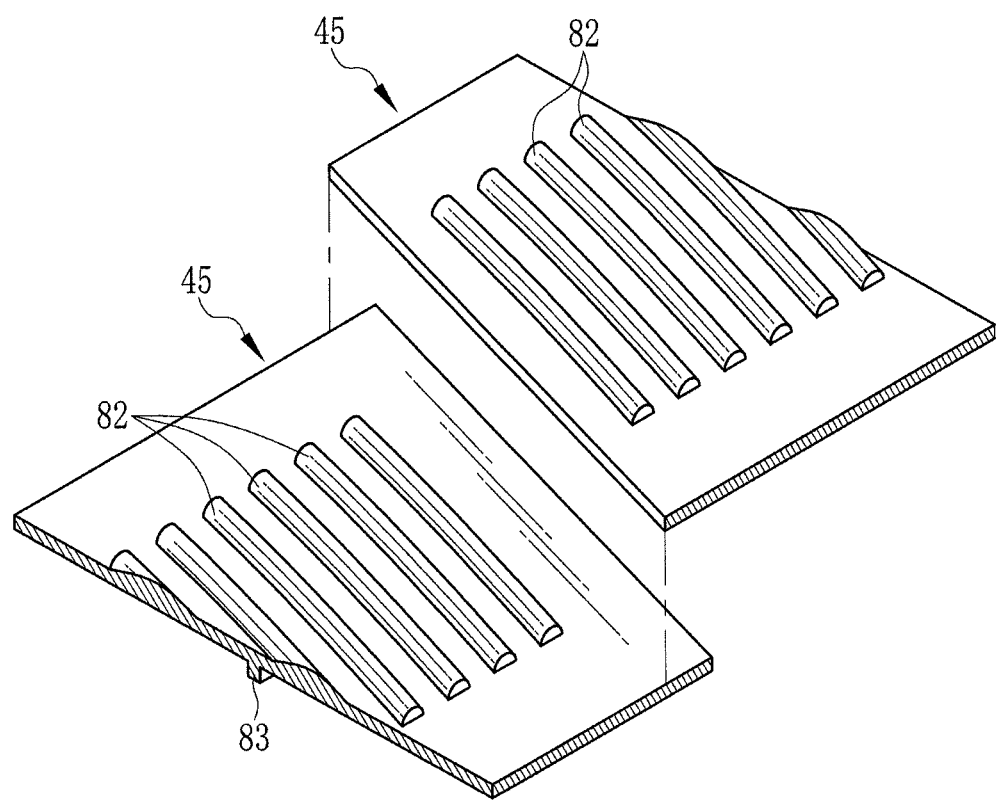
FIG. 7 is a perspective view, partially broken, illustrating an endless track device in the course of preparation.
Figure 8:
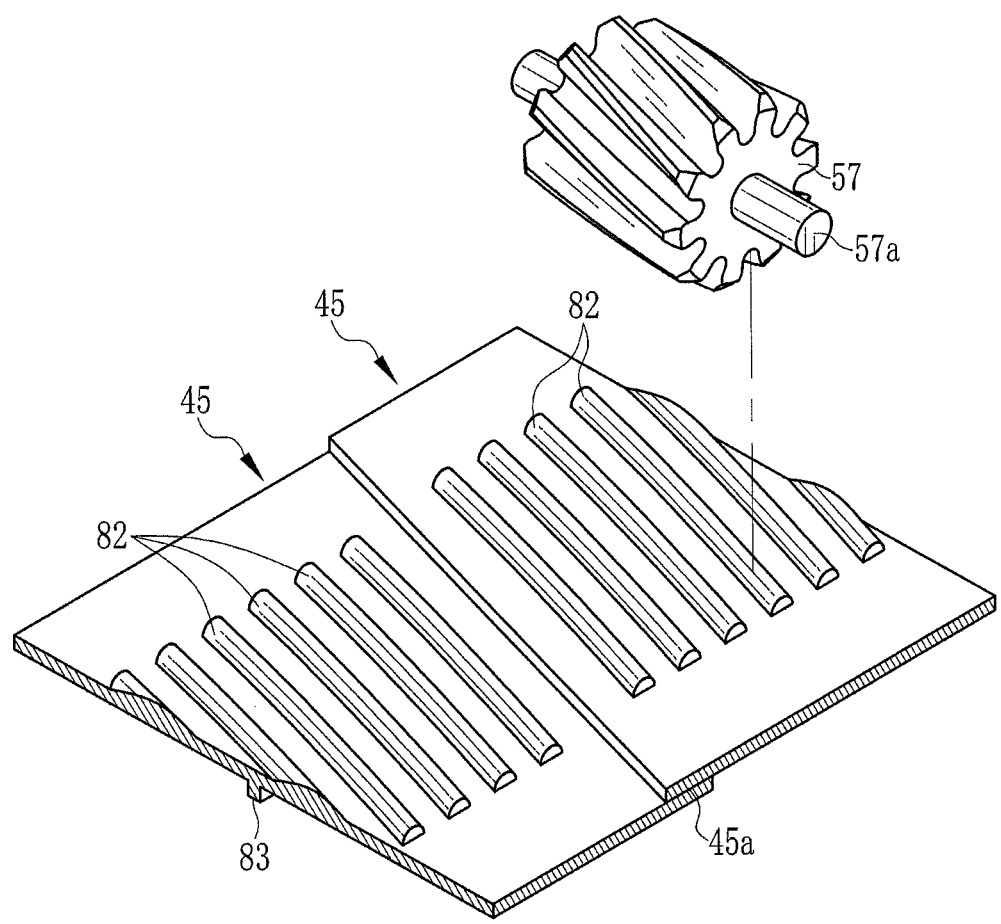
FIG. 8 is a perspective view, partially broken, illustrating the endless track device in a completed form with a worm wheel.
Figure 9:
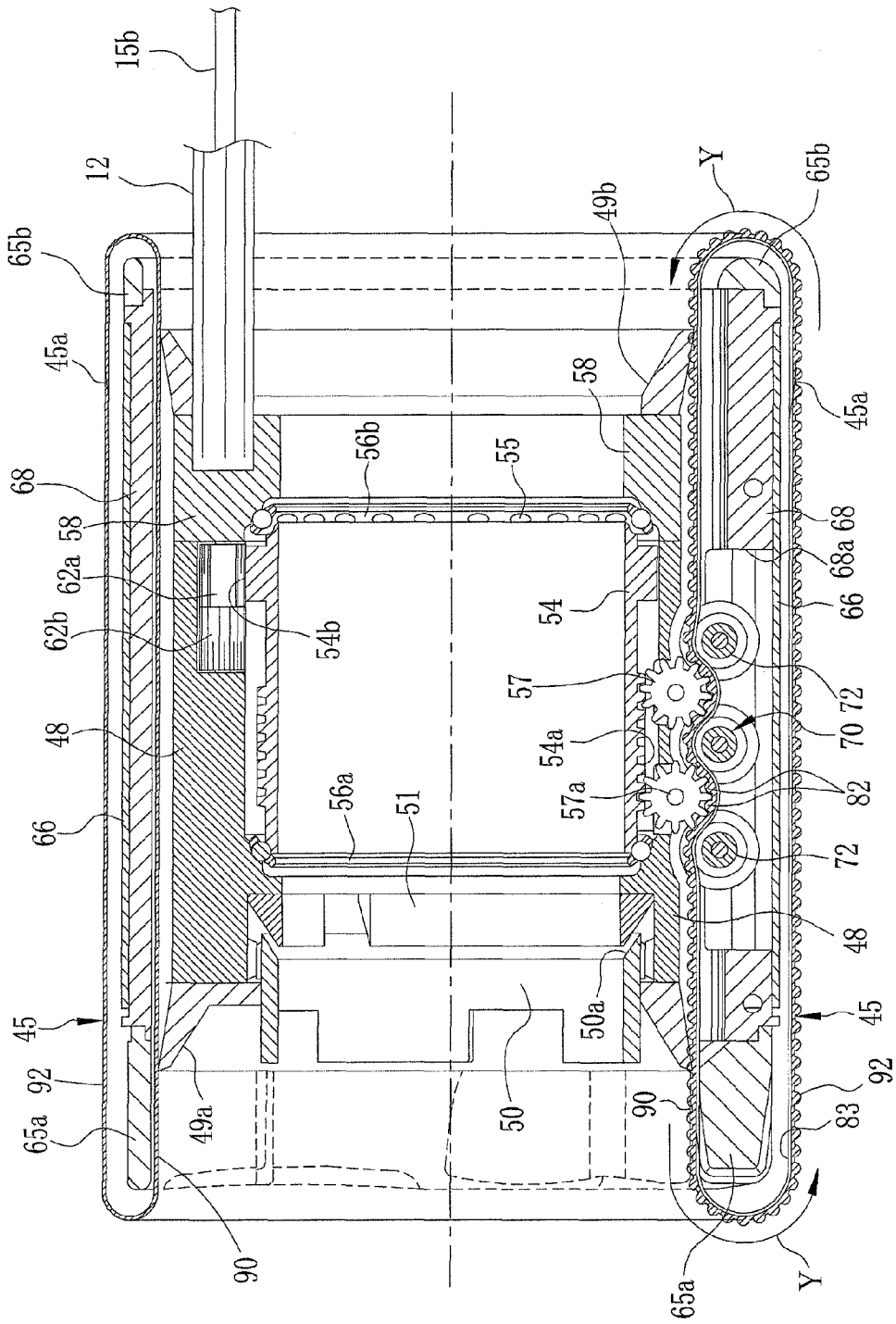
FIG. 9 is a vertical section illustrating the propulsion assembly.

The sleeve of the endless track device 45 in a developed form is positioned between the drive and barrel units 46 and 47. Those units are combined with one another. In FIGS. 7 and 8, ends of the sleeve of the endless track device 45 are turned over and connected with one another. A joint portion 45a of the endless track device 45 is formed. Note that inclinations can be preferably formed with ends of the sleeve of the endless track device 45, so that the joint portion 45a can have a small thickness without an excessive unevenness of the thickness. In FIG. 9, an assembled structure of the propulsion assembly 2 is schematically illustrated. The endless track device 45 can have an inner space to wrap the barrel unit 47 entirely in the toroidal shape. It is possible to fill the inner space with suitable fluid, such as air, physiological saline water, colloid of synthetic resin, oil, grease, lubricant fluid of various types, and the like.

Figure 10:
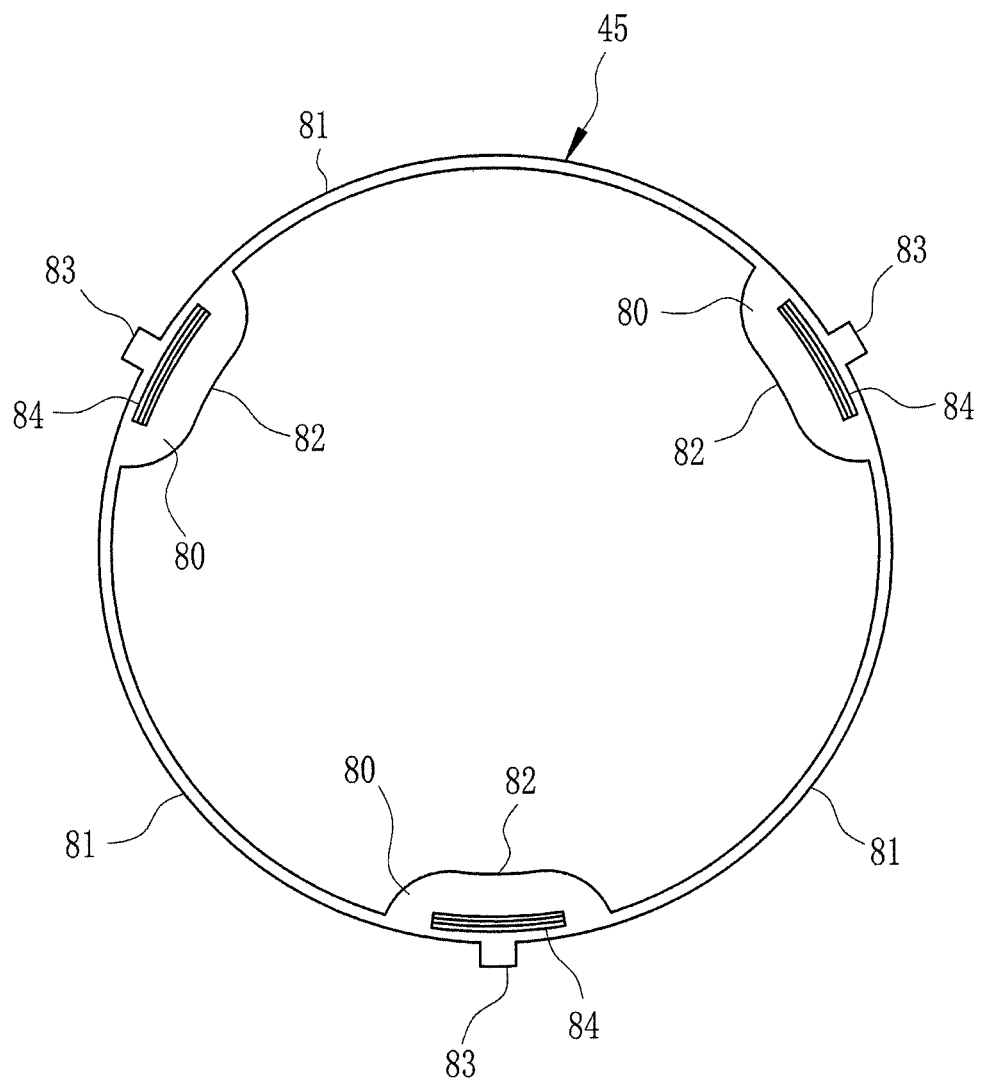
FIG. 10 is a cross section illustrating the endless track device.
Figure 11:
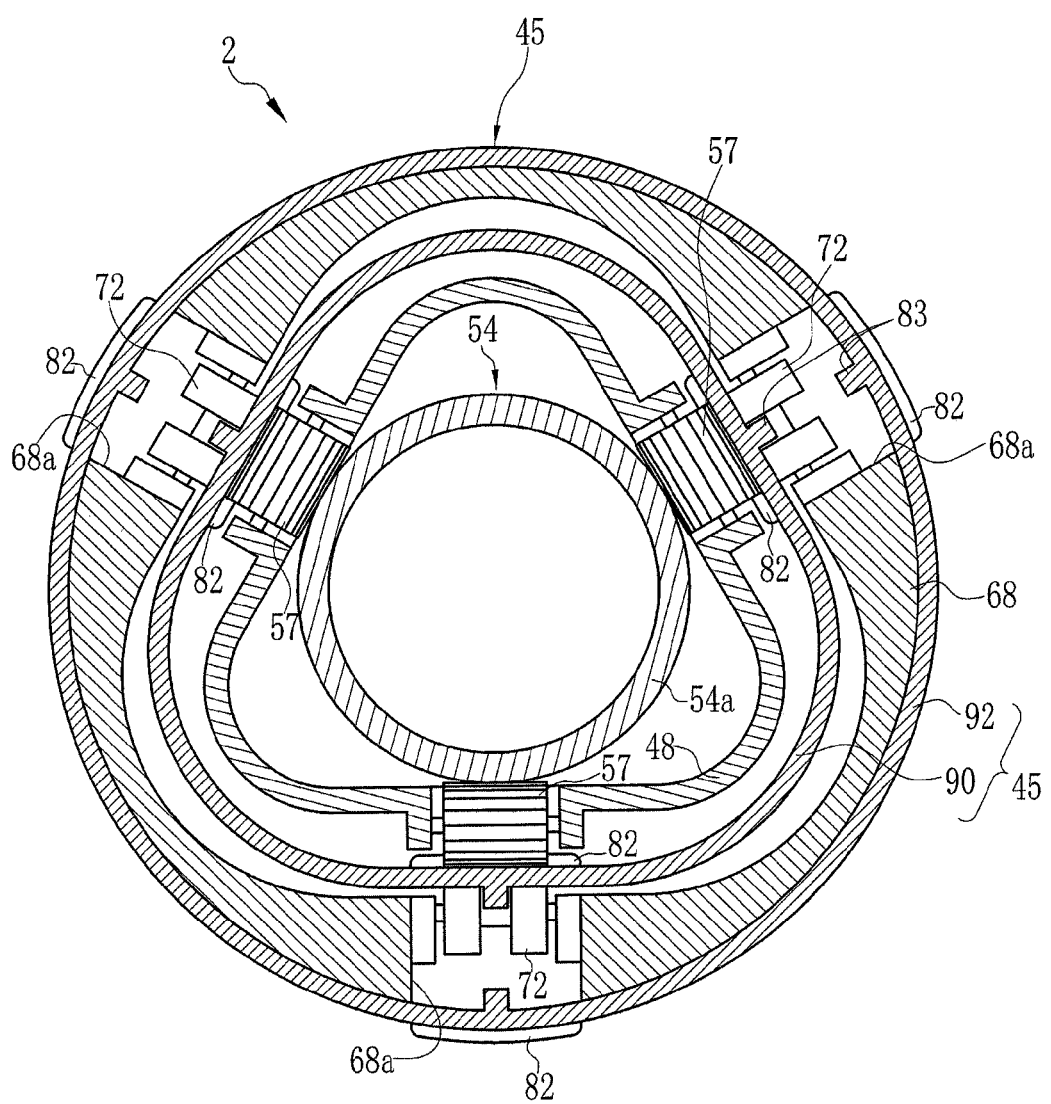
FIG. 11 is a cross section illustrating the propulsion assembly.

In FIGS. 7-11, the endless track device 45 is constituted by a multi-layer sheet of polyurethane resin or the like with plural film layers. Three reinforcing ridges 80 are formed on an inner sleeve surface of a sleeve for the endless track device 45, arranged equiangularly from one another, and formed in a trapezoidal shape as viewed in section. The reinforcing ridges 80 have a larger thickness than a membrane wall 81, and are constituted by a sheet of plural film layers of a higher number than those in the membrane wall 81. The reinforcing ridges 80 extend longitudinally in the axial direction. Engaging teeth 82 or rack gear teeth are disposed on the surface of the reinforcing ridges 80, and arranged with an inclination for mesh with the worm wheels 57. The engaging teeth 82 have a surface curved arcuately for contact with a wall of the body cavity where the tip device 3 moves in. In FIG. 10, the thickness of the reinforcing ridges 80 is emphasized.

Alignment ridges 83 are formed on the endless track device 45, extend longitudinally, and are opposite to the reinforcing ridges 80. Also, a mesh sheet 84 of fiber is disposed between the engaging teeth 82 and each of the alignment ridges 83.

The endless track device 45 is used in the toroidal shape in FIG. 9. The three reinforcing ridges 80 are nipped between the worm wheels 57 and the idler rollers 72. The worm wheels 57 are meshed with the engaging teeth 82. Rotation of the worm wheels 57 is transmitted directly to the endless track device 45 by the engaging teeth 82. The endless track device 45 can turn around efficiently in the axial direction. The reinforcing ridges 80 and also the mesh sheet 84 are in the multi-layer form. The engaging teeth 82 in the endless track device 45 can have sufficient mechanical strength even upon receiving driving force directly from the worm wheels 57, because the engaging teeth 82 do not deform or the endless track device 45 does not break. Also, the membrane wall 81 disposed beside the reinforcing ridges 80 is effective in reducing resistance of the endless track device 45 during passage between the drive and barrel units 46 and 47.

Roller grooves are formed in respectively the idler rollers 72 at the center. The alignment ridges 83 disposed opposite to the reinforcing ridges 80 are engaged with the roller grooves when the endless track device 45 moves. Note that the barrel unit 47 can be constructed in an adjustable form for reducing the inner space of the endless track device 45 in a tightly wrapped condition. In this form, the alignment ridges 83 are engaged also with the grooves 75a and 75b of the support rings 65a and 65b. See FIG. 4. The alignment ridges 83 are effective in stabilizing the path of the movement, as the endless track device 45 can be prevented from shifting in a zigzag manner while moved in the axial direction.

Figure 12:
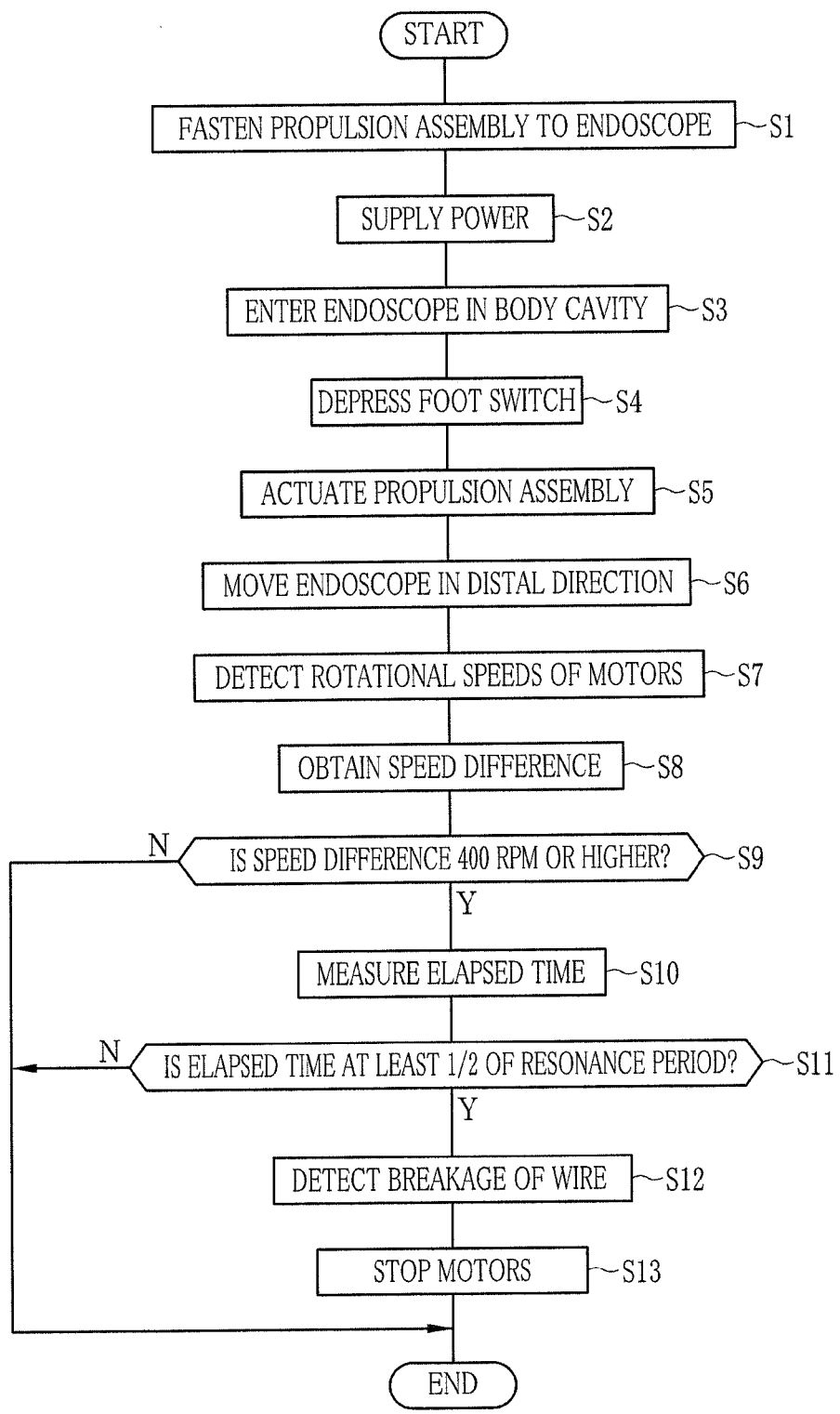
FIG. 12 is a flow chart illustrating propulsion with the propulsion assembly.

The operation of the above embodiment is described now. In FIG. 12, the propulsion assembly 2 is mounted on the endoscope in a state of protruding a distal end of the tip device 3 partially. A special screw driving device is used for mounting the propulsion assembly 2. The clamping sleeve 50 of the sealing device is rotated by the screw driving device in the clockwise direction. The clamping sleeve 50 is helically engaged with a female thread formed inside the support sleeve 48 on the distal side. Rotation of the clamping sleeve 50 in the clockwise direction shifts the clamping sleeve 50 in the inward direction or proximal direction. The tapered end surface 50a presses the sealing device 51 or C-ring. A tapered surface on a distal side of the sealing device 51 is pressed by the tapered end surface 50a to deform the sealing device 51 to decrease its diameter. The tip device 3 is squeezed by the sealing device 51 inside the support sleeve 48 upon the deformation. The propulsion assembly 2 is fastened to the tip device 3 reliably. See the step S1.

Then the wire sheath 12 extending from the proximal end of the propulsion assembly 2 is positioned along the outer surface of the steering device and the flexible device of the endoscope. Plural indicia are disposed on the wire sheath 12 equidistantly from one another, and indicate positions of attachment of the adhesive tape 4. The wire sheath 12 is attached to the steering device and the flexible device by use of the adhesive tape 4 according to the indicia. The key coupling device 17 at the proximal end of the wire sheath is plugged to the rotating coupling 18 for connection to the actuating assembly 10, which is powered. The actuating assembly 10 checks whether the key coupling device 17 is plugged to the rotating coupling 18 or not upon powering. If it is judged that the plugging is improper or if the plugging is not detected, alarm information is emitted, for example, alarm sound or a visible alarm signal with light. If it is judged that the plugging is proper, a sensor in the rotating coupling 18 reads type information of the propulsion assembly 2 from a signal region disposed on a bridge portion of the key coupling device 17. According to the type information, the actuating assembly 10 automatically determines a rotational speed of the wire devices 15a and 15b and a value of a torque limiter, and prevents the wire devices 15a and 15b from operating at too high a speed or torque. See the step S2.

When the power source is turned on, the actuating assembly 10 receives type information of the endoscope in connection with the processing apparatus 8 in a form of an output signal. The actuating assembly 10 includes an inner storage medium. The actuating assembly 10 recognizes the type information of the endoscope for use and type information of the propulsion assembly 2 by referring to table data stored in the storage medium. The table data is data of types of the endoscope and usable types of the propulsion assembly 2 in association with the endoscope types. For example, a shiftable range of the sealing device 51 is determined according to the type information of the propulsion assembly 2. An outer diameter of the tip device 3 is determined according to the type information of the endoscope. It is possible promptly to check whether the propulsion assembly 2 can be properly used in connection with the tip device 3 of the endoscope. If it is judged that a combination of the propulsion assembly 2 with the tip device 3 is improper, an alarm signal is generated, for example, alarm sound or visible alarm sign of light with an alarm lamp. Also, operation of the propulsion assembly 2 may be inhibited. Those functions can prevent occurrence of accidents.

When the propulsion assembly 2 is ready, the tip device 3 of the endoscope is entered in a gastrointestinal tract of a patient in the step S3, for example, large intestine. The foot switch 11 in connection with the actuating assembly 10 is depressed in the step S4. The speed signal generator 31 sends a speed signal to the speed servo amplifier 32 according to the control of the CPU 24 through the D/A converter 36 for a set rotational speed of the motors. The speed servo amplifier 32 sends a torque signal to the first and second current amplifiers 33a and 33b according to the speed signal. The first and second current amplifiers 33a and 33b send current signals to the drive amplifiers 37a and 37b in the drive circuit board 22 according to the torque signal.

The drive amplifiers 37a and 37b (drive devices) supply the first and second motors 19a and 19b with currents according to the input current signals. In response, the first and second motors 19a and 19b are driven to rotate the wire devices 15a and 15b. The coupling gears 62a and 62b rotate to cause the drive sleeve 54 to rotate by means of the spur gear teeth 54b meshed with the first coupling gear 62a. The second coupling gear 62b rotates in a direction reverse to that of the first coupling gear 62a, to which rotations of the second coupling gear 62b are transmitted directly. Consequently, the drive sleeve 54 can be rotated by both of the first and second motors 19a and 19b in the actuating assembly 10.

When the worm gear teeth 54a of the drive sleeve 54 rotate, the worm wheels 57 rotate in the same direction about respectively the gear shaft 57a. The endless track device 45 is tensioned between the teeth of the worm wheels 57 and the idler rollers 72 of the roller mechanisms 70. Also, the worm wheels 57 are meshed with the engaging teeth 82 of the endless track device 45. The idler rollers 72 are caused to rotate by the worm wheels 57 to move the endless track device 45 endlessly in the axial direction of the drive sleeve 54. In FIG. 9, the worm wheels 57 rotate in the clockwise direction. The idler rollers 72 rotate in the counterclockwise direction. A return run 90 of the endless track device 45 inside the barrel unit 47 moves from the proximal side to the distal side. A working run 92 of the endless track device 45 outside the barrel unit 47 moves from the distal side to the proximal side. Thus, the endless track device 45 endlessly turns around in the direction Y in the step S5.

The working run 92 of the endless track device 45 contacts a wall of the large intestine in entry of the endoscope with the propulsion assembly 2 in the gastrointestinal tract. While the endless track device 45 endlessly moves, propulsion force for advancing the tip device 3 is obtained, in other words, force for pressing the wall of the large intestine in the proximal direction is obtained. See the step S6.

During the distal movement of the endoscope, foreign material stuck on the working run 92 of the endless track device 45 may move toward the position of the return run 90 after passing the proximal end of the barrel unit 47. However, the flange edge of the proximal cover flange 49b is positioned very close to the endless track device 45 and prevents the foreign material from internal jamming. Also, the proximal cover flange 49b prevents tissue of a body part from internal jamming together with the endless track device 45. Note that during the proximal movement of the endoscope, the flange edge of the distal cover flange 49a operates in the same manner for protection.

Light from the light source apparatus 7 is guided by the universal cable 6, a light guide device of fiber inside the endoscope, and lighting windows, and applied to the wall of the large intestine. The CCD in the tip device 3 images the wall and outputs an image signal. An output cable in the endoscope and the universal cable 6 transmit the image signal to the processing apparatus 8, to drive the display panel 9 to display an object image of the wall. A doctor or operator views the large intestine with the display panel 9.

If a lesion is discovered in the imaging, he or she enters a treatment device suitable for the lesion through an instrument channel in the endoscope. The treatment device protrudes from a distal instrument opening (not shown), and treats the lesion.

Figure 13:
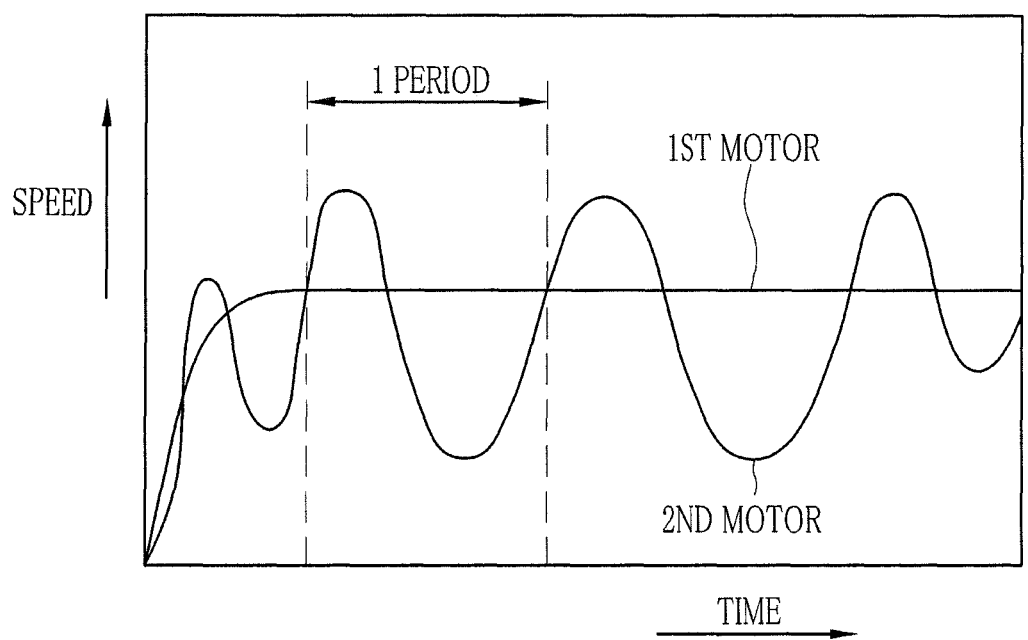
FIG. 13 is a graph illustrating changes in rotational speeds of motors.

In FIG. 13, the first tachogenerator 25a detects a rotational speed of the first motor 19a. The second tachogenerator 25b detects a rotational speed of the second motor 19b. See the step S7. The monitoring unit 26 for safety detects a speed difference between the rotational speeds of the first and second motors 19a and 19b in the step S8.

The first and second motors 19a and 19b rotate at an equal rotational speed (set rotational speed) upon supply of an equal current on a normal condition of the wire devices 15a and 15b without breakage.

If the first wire device 15a is broken, the rotational speed of the first motor 19a becomes higher than the set rotational speed owing to a smaller rotational load. The speed servo amplifier 32 supplies the first and second current amplifiers 33a and 33b with a torque signal of a smaller torque than before according to the feedback control. Thus, the rotational speed of the first motor 19a becomes decreased to the set rotational speed. When the first wire device 15a is broken, rotations of the first motor 19a are not transmitted to the first coupling gear 62a. The second motor 19b rotates to cause the first coupling gear 62a to rotate by use of the second wire device 15b and the second coupling gear 62b. This raises rotational load to the second motor 19b. However, the second motor 19b is driven with the lowered torque equal to that for the first motor 19a. Thus, the first coupling gear 62a with high resistance cannot be rotated, or can be rotated only slowly. The second motor 19b stops, or rotates slowly. As a result, the speed difference occurs between the first and second motors 19a and 19b.

If the second wire device 15b is broken, the rotational speed of the first motor 19a is decreased by an increase in the rotational load. Then the speed servo amplifier 32 inputs a torque signal of a higher torque than the present torque to the first and second current amplifiers 33a and 33b according to the feedback control. The rotational speed of the first motor 19a increases and becomes as high as the set rotational speed. The rotational speed of the second motor 19b becomes higher than the set rotational speed. There occurs a difference between the rotational speeds of the first and second motors 19a and 19b.

When the speed difference from the monitoring unit 26 becomes equal to or higher than 400 rpm as the reference speed value (yes in the step S9), the CPLD 23 starts a corresponding one of the counters 30a and 30b (timers) to measure elapsed time in the step S10. When the elapsed time becomes equal to or longer than a half of the resonance period (yes in the step S11), the CPLD 23 as a break detector recognizes that one of the wire devices 15a and 15b has been broken in the step S12.

A change in the speed of the first and second motors 19a and 19b may be created by resonance vibration of the wire devices 15a and 15b with the first and second motors 19a and 19b. Let the first and second motors 19a and 19b have a moment of inertia of $J=1\times10^{-5}$ kg·m$^2$. Let the wire devices 15a and 15b have torsional rigidity of $K=1\times10^{-4}$ N·m/rad. A resonant frequency of the resonance vibration is $f=1/(2\pi)\times(K/J)^{1/2}=0.5$ Hz. A resonance period of the resonance vibration is $T=1/f=2$ sec. The speed difference due to the resonance vibration of the wire devices is canceled by the feedback control at a short time smaller than one second, namely a half of the resonance period T of the resonance vibration. If the elapsed time of occurrence of the speed difference becomes equal to or longer than one second (T/2), it is judged that breakage of the wire device has occurred. In short, no breakage is detected only upon occurrence of a speed difference due to the resonance vibration of the wire devices. It is possible reliably to prevent misdetection of breakage in comparison with a detection method of detecting breakage simply when a speed difference becomes equal to or more than 400 rpm. Operability of the propulsion can be maintained.

Upon detecting the breakage, the CPLD 23 supplies the drive amplifiers 37a and 37b in the drive circuit board 22 with a stop signal. In response, the drive amplifiers 37a and 37b stop supplying a current to the first and second motors 19a and 19b, which are stopped in the step S13. At the same time, the CPLD 23 drives the display panel 9 to display information of detected breakage as an alarm device.

If the operator wishes to remove the propulsion assembly 2 from the tip device 3, the clamping sleeve 50 is rotated in the counterclockwise direction by use of the screw driving device. The clamping sleeve 50 shifts in an outward direction by rotating, and releases the sealing device 51 from being pressed. The sealing device 51 is enlarged by its resiliency to separate its inner surface from an outer surface of the tip device 3. The propulsion assembly 2 can be removed from the endoscope easily.

In the above embodiment, the motors are stopped upon detecting breakage. However, control of various types can be carried out after detecting the breakage. For example, the motors can be driven to remove the endoscope from the body by moving the tip device 3 in the proximal direction.

The structure of the embodiment is effective in detecting breakage of one of the wire devices 15a and 15b. The counters 30a and 30b do not operate simultaneously for measuring time. It is possible to incorporate only one counter in the monitoring unit 26, and to input signals from the comparators 29a and 29b to the counter for measuring time.

In the above embodiment, the propulsion apparatus moves the tip device 3 of the endoscope forwards and backwards. However, a propulsion apparatus of the invention can be a type for moving the tip device 3 of the endoscope at least forwards or in the distal direction.

In the above embodiments, the endless track device is in a toroidal shape. However, an endless track device of the invention may include a plurality of endless belts arranged in a circumferential direction of the barrel unit and extending in the axial direction.

Furthermore, the present invention is not limited to the propulsion apparatus. A drive apparatus according to the invention can be a type other than the propulsion apparatus for a purpose of assisting the operation of the endoscope, with a structure including a drive assembly externally set on the tip device of the endoscope, and two wire devices for actuating the drive assembly.

In the above embodiments, the endoscope is for a medical use. However, an endoscope of the invention can be one for industrial use, a probe of an endoscope, or the like for various purposes.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A propulsion apparatus for an endoscope, comprising:
   a propulsion assembly for mounting on a tip device of said endoscope, for propulsion in a body cavity;
   first and second wire devices, disposed to extend from said tip device in a proximal direction, for driving said propulsion assembly;
   first and second motors, connected with proximal ends of said first and second wire devices, respectively, for generating torque for actuating said propulsion assembly;
   a monitoring unit, actuated if a speed difference between said first and second motors becomes equal to or more than a reference speed value, for measuring an elapsed time;
   a break detector for detecting breakage of said first or second wire device if said elapsed time becomes equal to or longer than a reference time; and
   a controller for controlling said first and second motors in response to detection of said break detector,
   wherein said monitoring unit includes:
      a speed measuring device for measuring rotational speeds of said first and second motors;
      a combining circuit for acquiring said speed difference arithmetically;
      a first comparator for detecting said speed difference being equal to or more than said reference speed value in relation to breakage of said first wire device; and
      a first timer for measuring said elapsed time in response to an output of said first comparator,
   wherein said propulsion assembly includes:
      a support sleeve for receiving entry of said tip device;
      a barrel sleeve disposed around said support sleeve;
      an endless track device, disposed to extend along inner and outer surfaces of said barrel sleeve, for contacting a wall of said body cavity, and endlessly moving in an axial direction of said endoscope; and
      a driving mechanism, connected with said first and second wire devices, for driving said endless track device upon actuation of said first and second motors, and wherein the controller stops the first and second motors upon detection of a signal from the break detector.

2. A propulsion apparatus as defined in claim 1, wherein said first and second wire devices have a coil winding.

3. A propulsion apparatus as defined in claim 1, wherein said reference time is equal to or longer than a half of a resonance period of said first and second motors.

4. A propulsion apparatus as defined in claim 1, wherein said monitoring unit further includes:
an inverter for inverting a sign of said speed difference to obtain a second speed difference;
a second comparator for detecting said second speed difference being equal to or more than said reference speed value in relation to breakage of said second wire device;
a second timer for measuring said elapsed time in response to an output of said second comparator.

5. A propulsion apparatus as defined in claim 1, wherein if said first or second wire device is broken, said controller stops said first and second motors.

6. A propulsion apparatus as defined in claim 1, further comprising an alarm device for alarming upon detection of said breakage of said first or second wire device in said break detector.

7. A propulsion apparatus as defined in claim 4, further comprising:
a first drive device for driving said first motor;
a second drive device for driving said second motor;
a servo control unit, connected with said speed measuring device, for feedback control of said first and second drive devices according to said rotational speeds being measured.

8. A propulsion apparatus as defined in claim 1, wherein said endless track device is disposed to extend circumferentially around said barrel sleeve in a toroidal form.

9. A propulsion apparatus as defined in claim 1, wherein said endless track device includes a plurality of endless belts disposed to cover said barrel sleeve partially.

10. A propulsion apparatus as defined in claim 1, wherein said propulsion assembly includes:
a drive sleeve, contained in said support sleeve in a rotatable manner, and having spur gear teeth formed on an outer surface thereof;
first and second coupling gears, connected with distal ends of respectively said first and second wire devices, for rotating said drive sleeve with said spur gear teeth.

11. A propulsion apparatus as defined in claim 10, wherein said propulsion assembly further includes a sealing device for fastening said support sleeve to said tip device of said endoscope.

12. A propulsion apparatus as defined in claim 10, wherein said propulsion assembly includes a plurality of idler rollers, supported on said barrel sleeve in a rotatable manner, for contacting an internal surface of said endless track device;
said driving mechanism includes:
worm gear teeth formed on said outer surface of said drive sleeve;
a plurality of wheels, supported on said support sleeve in a rotatable manner, meshed with said worm gear teeth, for driving said endless track device contacted by said idler rollers.

13. A drive apparatus for an endoscope, comprising:
a drive assembly for mounting on a tip device of said endoscope;
first and second wire devices, disposed to extend from said tip device in a proximal direction, for driving said drive assembly;
first and second motors, connected with proximal ends of said first and second wire devices, respectively, for generating torque for actuating said drive assembly;
a monitoring unit, actuated if a speed difference between said first and second motors becomes equal to or more than a reference speed value, for measuring an elapsed time;
a break detector for detecting breakage of said first or second wire device if said elapsed time becomes equal to or longer than a predetermined time;
a controller for controlling said first and second motors in response to detection of said break detector,
wherein said monitoring unit includes:
a speed measuring device for measuring rotational speeds of said first and second motors;
a combining circuit for acquiring said speed difference arithmetically;
a first comparator for detecting said speed difference being equal to or more than said reference speed value in relation to breakage of said first wire device; and
a first timer for measuring said elapsed time in response to an output of said first comparator,
wherein said propulsion assembly includes:
a support sleeve for receiving entry of said tip device;
a barrel sleeve disposed around said support sleeve;
an endless track device, disposed to extend along inner and outer surfaces of said barrel sleeve, for contacting a wall of said body cavity, and endlessly moving in an axial direction of said endoscope; and
a driving mechanism, connected with said first and second wire devices, for driving said endless track device upon actuation of said first and second motors, and
wherein the controller stops the first and second motors upon detection of a signal from the break detector.

* * * * *